United States Patent
Bonnette et al.

(10) Patent No.: US 7,169,161 B2
(45) Date of Patent: *Jan. 30, 2007

(54) GUIDEWIRE HAVING OCCLUSIVE DEVICE AND REPEATABLY CRIMPABLE PROXIMAL END

(75) Inventors: Michael J. Bonnette, Minneapolis, MN (US); Eric J. Thor, Arden Hills, MN (US); Mark L. Jenson, Greenfield, MN (US); Rick C. Kravic, Champlin, MN (US); Hieu V. Le, Brooklyn Park, MN (US)

(73) Assignee: Possis Medical, Inc., Minneapolis, MN (US)

( * ) Notice: Subject to any disclaimer, the term of this patent is extended or adjusted under 35 U.S.C. 154(b) by 327 days.

This patent is subject to a terminal disclaimer.

(21) Appl. No.: 10/012,891

(22) Filed: Nov. 6, 2001

(65) Prior Publication Data

US 2003/0088262 A1    May 8, 2003

(51) Int. Cl.
*A61M 25/10* (2006.01)
(52) U.S. Cl. ............ 606/191; 606/192; 606/194; 604/96.01; 604/99.01
(58) Field of Classification Search ........ 606/191–200, 606/159, 108, 168, 166; 600/585; 604/96.01–103
See application file for complete search history.

(56) References Cited

U.S. PATENT DOCUMENTS

| | | | |
|---|---|---|---|
| 4,573,470 A | 3/1986 | Samson et al. | |
| 4,573,966 A | 3/1986 | Weikl et al. | |
| 4,636,195 A | 1/1987 | Wolinsky | |
| 4,646,719 A | 3/1987 | Neuman et al. | |
| 4,733,652 A | 3/1988 | Kantrowitz et al. | |
| 4,832,023 A * | 5/1989 | Murphy-Chutorian et al. . | 606/7 |
| 4,838,268 A | 6/1989 | Keith et al. | |
| 4,865,587 A | 9/1989 | Walling | |
| 5,059,176 A | 10/1991 | Winters | |
| 5,059,178 A | 10/1991 | Ya | |
| 5,135,482 A | 8/1992 | Neracher | |
| 5,167,239 A | 12/1992 | Cohen et al. | |
| 5,171,221 A | 12/1992 | Samson | |
| 5,176,692 A * | 1/1993 | Wilk et al. .................. | 606/151 |
| 5,195,955 A | 3/1993 | Don Michael | |
| 5,209,727 A | 5/1993 | Radisch, Jr. et al. | |
| 5,320,604 A | 6/1994 | Walker et al. | |
| 5,380,284 A | 1/1995 | Don Michael | |
| 5,520,645 A | 5/1996 | Imran et al. | |
| 5,584,843 A * | 12/1996 | Wulfman et al. ........... | 606/159 |
| 5,688,234 A | 11/1997 | Frisbie | |
| 5,713,917 A | 2/1998 | Leonhardt et al. | |
| 5,775,327 A | 7/1998 | Randolph et al. | |
| 5,776,100 A | 7/1998 | Forman | |

(Continued)

*Primary Examiner*—Michael J. Hayes
*Assistant Examiner*—Michael G. Mendoza
(74) *Attorney, Agent, or Firm*—Hugh D. Jaeger, Esq.

(57) ABSTRACT

A tubular guidewire assembly having a distal occlusive device and an extended crimpable section proximate a proximal end that is adapted to connect to a gas inflation/evacuation system. The extended crimpable section can be selectively sealed at one of a plurality of separate locations to form an airtight seal of the tubular guidewire assembly. Each time a deflation of the occlusive device is desired in order to reestablish blood flow to a vessel downstream of the occlusive device, the extended crimpable section preferably is cut distal to the location of the last seal to quickly deflate the occlusive device.

23 Claims, 8 Drawing Sheets

U.S. PATENT DOCUMENTS

| | | | |
|---|---|---|---|
| 5,779,688 A | 7/1998 | Imran et al. | |
| 5,792,179 A | 8/1998 | Sideris | |
| 5,807,330 A | 9/1998 | Teitelbaum | |
| 5,827,324 A | 10/1998 | Cassell et al. | |
| 5,833,644 A | 11/1998 | Zadno-Azizi et al. | |
| 5,833,650 A | 11/1998 | Imran | |
| 5,843,022 A | 12/1998 | Willard et al. | |
| 5,865,721 A | 2/1999 | Andrews et al. | |
| 5,882,335 A * | 3/1999 | Leone et al. | 604/103.02 |
| 5,908,405 A | 6/1999 | Imran et al. | |
| 5,925,016 A | 7/1999 | Chornenky et al. | |
| 5,938,672 A | 8/1999 | Nash | |
| 5,997,558 A | 12/1999 | Nash | |
| 6,021,340 A | 2/2000 | Randolph et al. | |
| 6,022,336 A | 2/2000 | Zadno-Azizi et al. | |
| 6,036,715 A * | 3/2000 | Yock | 606/194 |
| 6,050,972 A | 4/2000 | Zadno-Azizi et al. | |
| 6,080,170 A | 6/2000 | Nash et al. | |
| 6,135,991 A | 10/2000 | Muni et al. | |
| 6,146,372 A | 11/2000 | Leschinsky et al. | |
| 6,159,195 A | 12/2000 | Ha et al. | |
| 6,171,328 B1 | 1/2001 | Addis | |
| 6,176,844 B1 | 1/2001 | Lee | |
| 6,203,561 B1 | 3/2001 | Ramee et al. | |
| 6,217,567 B1 | 4/2001 | Zadno-Azizi et al. | |
| 6,231,588 B1 | 5/2001 | Zadno-Azizi | |
| 6,241,706 B1 | 6/2001 | Leschinsky et al. | |
| 6,428,559 B1 * | 8/2002 | Johnson | 606/200 |
| 6,554,795 B2 * | 4/2003 | Bagaoisan et al. | 604/103.11 |
| 6,575,958 B1 * | 6/2003 | Happ et al. | 604/525 |
| 6,932,828 B2 * | 8/2005 | Bonnette et al. | 606/194 |
| 6,942,678 B2 * | 9/2005 | Bonnette et al. | 606/191 |
| 2001/0014821 A1 * | 8/2001 | Juman et al. | 623/1.11 |
| 2002/0062119 A1 * | 5/2002 | Zadno-Azizi | 604/509 |
| 2002/0072705 A1 * | 6/2002 | Vrba et al. | 604/96.01 |
| 2002/0095137 A1 * | 7/2002 | Zadno-Azizi et al. | 604/530 |
| 2002/0173817 A1 * | 11/2002 | Kletschka et al. | 606/194 |

* cited by examiner

GUIDEWIRE HAVING OCCLUSIVE DEVICE AND REPEATABLY CRIMPABLE PROXIMAL END

RELATED APPLICATIONS

The present invention is related to two co-pending applications that are commonly assigned to the assignee of the present invention and filed concurrently herewith, the first of which is entitled "Guidewire Occlusion System Utilizing Repeatably Inflatable Gas-filled Occlusive Device," application Ser. No. 10/012,903, and the second of which is entitled "Gas Inflation/Evacuation System and Sealing System for Guidewire Assembly Having Occlusive Device," application Ser. No. 10/007,788, a copy of each of which is attached and the disclosures of both of which are incorporated by reference.

FIELD OF THE INVENTION

The present invention relates generally to the field of vascular medical devices. More specifically, the present invention relates to a guidewire assembly with a repeatably inflatable gas-filled distal occlusive device and a repeatably crimpable proximal end for use with a guidewire occlusion system in vascular procedures.

BACKGROUND OF THE INVENTION

Arterial disease involves damage that happens to the arteries in the body. Diseased arteries can become plugged with thrombus, plaque, or grumous material that may ultimately lead to a condition known as ischemia. Ischemia refers to a substantial reduction or loss of blood flow to the heart muscle or any other tissue that is being supplied by the artery and can lead to permanent damage of the affected region. While arterial disease is most commonly associated with the formation of hard plaque and coronary artery disease in the heart, similar damage can happen to many other vessels in the body, such as the peripheral vessels, cerebral vessels, due to the buildup of hard plaque or softer thrombus or grumous material within the lumen of an artery or vein.

A variety of vascular medical devices and procedures have been developed to treat diseased vessels. The current standard procedures include bypass surgery (where a new blood vessel is grafted around a narrowed or blocked artery) and several different types of non-surgical interventional vascular medical procedures, including angioplasty (where a balloon on a catheter is inflated inside a narrowed or blocked portion of an artery in an attempt to push back plaque or thrombotic material), stenting (where a metal mesh tube is expanded against a narrowed or blocked portion of an artery to hold back plaque or thrombotic material), and debulking techniques in the form of atherectomy (where some type of high speed or high power mechanism is used to dislodge hardened plaque) or thrombectomy (where some type of mechanism or infused fluid is used to dislodge grumous or thrombotic material). In each of these interventional vascular medical procedures, a very flexible guidewire is routed through the patient's vascular system to a desired treatment location and then a catheter that includes a device on the distal end appropriate for the given procedure is tracked along the guidewire to the treatment location.

Although interventional vascular procedures avoid many of the complications involved in surgery, there is a possibility of complications if some of the plaque, thrombus or other material breaks free and flows downstream in the artery or other vessel, potentially causing a stroke, a myocardial infarction (heart attack), or other tissue death. One solution to this potential complication is to use some kind of occlusive device to block or screen the blood flowing downstream of the treatment location. Examples of catheter arrangements that use a pair of balloons as occlusive devices to create an isolated space in the blood vessel are described in U.S. Pat. Nos. 4,573,966, 4,636,195, 5,059,178, 5,320, 604, 5,833,644, 5,925,016, 6,022,336 and 6,176,844. Examples of catheter arrangements that use a single balloon as an occlusive device either upstream or downstream of the treatment location are described in U.S. Pat. Nos. 5,171,221, 5,195,955, 5,135,482, 5,380,284, 5,688,234, 5,713,917, 5,775,327, 5,792,179, 5,807,330, 5,833,650, 5,843,022, 6,021,340, 6,159,195 and 6,248,121. An example of a catheter arrangement that uses a mechanically-expanded occlusive device is shown in U.S. Pat. No. 6,231,588. Occlusive balloons also have been used on non-over-the-wire catheters without any guidewire internal to the catheter as described, for example, in U.S. Pat. Nos. 4,838,268 and 5,209,727.

The use of an occlusive device as part of a vascular procedure is becoming more common in debulking procedures performed on heart bypass vessels. Most heart bypass vessels are harvested and transplanted from the saphenous vein located along the inside of the patient's leg. The saphenous vein is a long, straight vein that has a capacity more than adequate to support the blood flow needs of the heart. Once transplanted, the saphenous vein is subject to a buildup of plaque or thrombotic materials in the grafted arterial lumen. Unfortunately, the standard interventional vascular treatments for debulking are only moderately successful when employed to treat saphenous vein coronary bypass grafts. The complication rate for a standard balloon angioplasty procedure in a saphenous vein coronary bypass graft is higher than in a native vessel with the complications including embolization, "no-reflow" phenomena, and procedural related myocardial infarction. Atherectomy methods including directional, rotational, and laser devices are also associated with a high degree of embolization resulting in a greater likelihood of infarction. The use of stents for saphenous vein coronary bypass grafts has produced mixed results. Stents provide for less restenosis, but they do not eliminate the risk of embolization and infarction incurred by standard balloon angioplasty.

In order to overcome the shortcomings of these standard non-surgical interventional treatments in treating saphenous vein coronary bypass graft occlusion, embolic protection methods utilizing a protective device distal to the lesion have been developed. The protective device is typically a filter or a balloon. Use of a protective device in conjunction with an atherectomy or thrombectomy device is intended to prevent emboli from migrating beyond the protective device and to allow the embolic particles to be removed, thereby subsequently reducing the risk of myocardial infarction. When the occlusive device is a balloon, the balloon is inserted and inflated at a point distal to the treatment site or lesion site. Therapy is then performed at the treatment site and the balloon acts to block all blood flow which prevents emboli from traveling beyond the balloon. Following treatment, some form of particle removal device must be used to remove the dislodged emboli prior to balloon deflation. U.S. Pat. No. 5,843,022 uses a balloon to occlude the vessel distal to a lesion or blockage site. The occlusion is treated with a high pressure water jet, and the fluid and entrained emboli are subsequently removed via an extraction tube. U.S. Pat. No. 6,135,991 describes the use of a balloon to occlude the vessel allowing blood flow and pressure to prevent the migration of emboli proximally from the treatment device.

There are various designs that have included an occlusive balloon on the end of a guidewire. U.S. Pat. Nos. 5,520,645, 5,779,688 and 5,908,405 describe guidewires having removable occlusive balloons on a distal end. U.S. Pat. No. 4,573,470 describes a guidewire having an occlusive balloon where the guidewire is bonded inside the catheter as an integral unit. U.S. Pat. Nos. 5,059,176, 5,167,239, 5,520, 645, 5,779,688 and 6,050,972 describe various guidewires with balloons at the distal end in which a valve arrangement is used to inflate and/or deflate the balloon. U.S. Pat. No. 5,908,405 describes an arrangement with a removable balloon member that can be repeatedly inserted into and withdrawn from a guidewire. U.S. Pat. No. 5,776,100 describes a guidewire with an occlusive balloon adhesively bonded to the distal end with an adapter on the proximal end to provide inflation fluid for the occlusive balloon.

Except in the case of the normal cerebral anatomy where there are redundant arteries supplying blood to the same tissue, one of the problems with using an occlusive device in the arteries is that tissue downstream of the occlusive device can be damaged due to the lack of blood flow. Consequently, an occlusive device that completely blocks the artery can only be deployed for a relatively short period of time. To overcome this disadvantage, most of the recent development in relation to occlusive devices has focused on devices that screen the blood through a filter arrangement. U.S. Pat. Nos. 5,827,324, 5,938,672, 5,997,558, 6,080,170, 6,171,328, 6,203,561 and 6,245,089 describe various examples of filter arrangements that are to be deployed on the distal end of a catheter system. While a filter arrangement is theoretically a better solution than an occlusive device, in practice such filter arrangements often become plugged, effectively turning the filter into an occlusive device. The filter arrangements also are mechanically and operationally more complicated than an occlusive balloon device in terms of deployment and extraction.

As is the case in almost all angioplasty devices or stenting catheter devices where a balloon is used to expand the blood vessel or stent, most catheter occlusive balloons as well as most guidewire occlusive balloons utilize a liquid fluid such as saline or saline mixed with a radiopaque marker for fluoroscopic visualization (i.e., contrast) as the inflation medium. Generally, a liquid fluid medium for expanding vascular balloons has been preferred because the expansion characteristics of a liquid are more uniform and predictable, and because a liquid medium is easier to work with and more familiar to the doctors. In the case of angioplasty balloons, for example, high-pressure requirements (up to 20 atmospheres) necessitate that the inflation fluid be an incompressible fluid for safety reasons. While having numerous advantages, liquid fluids do not lend themselves to rapid deflation of an occlusive balloon because of the high resistance to movement of the liquid in a long small diameter tube. In the context of angioplasty procedures, the balloon catheter has a much larger lumen than a guidewire. Consequently, rapid deflation is possible. In the context of a guidewire, however, liquid filled occlusive balloons typically cannot be deflated in less than a minute and, depending upon the length of the guidewire, can take up to several minutes to deflate. Consequently, it is not practical to shorten the period of total blockage of a vessel by repeatedly deflating and then re-inflating a liquid filled occlusive balloon at the end of a guidewire.

Gas-filled balloons have been used for intra-aortic occlusive devices where rapid inflation and deflation of the occlusive device is required. Examples of such intra-aortic occlusive devices are shown in U.S. Pat. Nos. 4,646,719, 4,733,652, 5,865,721, 6,146,372, 6,245,008 and 6,241,706. While effective for use as an intra-aortic occlusive device, these occlusive devices are not designed for use as a guidewire as there is no ability to track a catheter over the intra-aortic occlusive device.

An early catheter balloon device that utilized a gas as an inflation medium and provided a volume limited syringe injection system is described in U.S. Pat. No. 4,865,587. More recently, a gas-filled occlusive balloon on a guidewire is described as one of the alternate embodiments in U.S. Pat. No. 6,217,567. The only suggestion for how the guidewire of the alternate embodiment is sealed is a valve type arrangement similar to the valve arrangement used in a liquid fluid embodiment. A similar gas-filled occlusive balloon has been described with respect to the Aegis Vortex™ system developed by Kensey Nash Corporation. In both U.S. Pat. No. 6,217,567 and the Aegis Vortex™ system, the gas-filled occlusive balloon is used for distal protection to minimize the risk of embolization while treating a blocked saphenous vein coronary bypass graft. Once deployed, the occlusive balloon retains emboli dislodged by the atherectomy treatment process until such time as the emboli can be aspirated from the vessel. No specific apparatus are shown or described for how the gas is to be introduced into the device or how the occlusive balloon is deflated.

Although the use of occlusive devices has become more common for distal embolization protection in vascular procedures, particularly for treating a blocked saphenous vein coronary bypass graft, all of the existing approaches have significant drawbacks that can limit their effectiveness. Liquid filled occlusive balloons can remain in place too long and take too long to deflate, increasing the risk of damages downstream of the occlusion. Occlusive filters are designed to address this problem, but suffer from blockage problems and can be complicated to deploy and retrieve and may allow small embolic particles to migrate downstream. Existing gas-filled occlusive balloons solve some of the problems of liquid filled occlusive balloons, but typically have utilized complicated valve and connection arrangements. It would be desirable to provide for an occlusive device that was effective, simple, quick to deploy and deflate, and that could overcome the limitations of the existing approaches.

SUMMARY OF THE INVENTION

The present invention is a tubular guidewire assembly having an extended crimpable section proximate a proximal end that is adapted to removably connect to a gas inflation/evacuation system and a sealing system. The extended crimpable section can be selectively sealed at one of a plurality of separate locations to form an airtight seal of the tubular guidewire assembly. Each time a deflation of the occlusive device is desired in order to reestablish blood flow to a vessel downstream of the occlusive device, the extended crimpable section preferably is cut distal to the location of the last seal to quickly deflate the occlusive device.

The advantage of the tubular guidewire assembly of the present invention is that the occlusive device can be repeatably inflated and deflated a plurality of times during a vascular procedure in between which the proximal end of the tubular guidewire assembly is free of mechanical connections and obstructions and, therefore, the tubular guidewire assembly can function as a conventional exchange guidewire assembly for one or more over-the-wire catheters. Alternatively, the tubular guidewire assembly of the present invention can be shorter in length for use with rapid exchange catheter systems. Unlike operation of existing liquid filled occlusive devices, the present invention enables repeated and quick inflation and deflation which allows an operator to deploy the gas-filled occlusive device numerous times during a procedure for shorter periods of time, thereby reducing the risk of potential damage to downstream tissue. Unlike operation of other gas-filled occlusive devices, the simplicity of the present invention permits the tubular guidewire assembly to be used as a conventional exchange guidewire assembly. There are no complicated mechanical arrangements or valve systems internal to the tubular guidewire assembly that increase the cost, complexity, and potential for failure of the system.

In a preferred embodiment, the extended crimpable section has a sufficient length to permit a plurality of crimps and cuts along the extended crimpable section and has an outer diameter that is smaller than the outer diameter of the main body portion of the guidewire assembly. A crimping mechanism is used to crimp the extended crimpable section of the guidewire assembly to seal the guidewire assembly a plurality of times. Each time a deflation of the occlusive device is desired in order to reestablish blood flow to the vessel downstream of the occlusive device, the extended crimpable section is cut distal to the location of the last crimp so as to quickly deflate the occlusive device. Preferably, the extended crimpable section of the guidewire assembly is dimensioned and the crimping mechanism is arranged such that an effective outer diameter of the extended crimpable section at the location of a seal is no greater than the outer diameter of the main body portion of the guidewire assembly when the extended crimpable section is sealed.

In one embodiment for coronary vascular procedures, the guidewire assembly preferably has an effective length of at least 40 cm and more preferably at least 100 cm and an outer diameter of less than 0.060 inch and more preferably less than 0.018 inch, the extended crimpable section has an effective length of at least 1 cm and more preferably at least cm and an outer diameter of less than 0.050 inch and more preferably less than 0.012 inch, and the occlusive device (balloon) is deflated in less than two minutes and more preferably less than one minute. This embodiment is particularly adapted to provide distal embolization protection in atherectomy procedures, such as those involving a blocked saphenous vein coronary bypass graft. Alternatively, the guidewire assembly may be configured and dimensioned for use in peripheral vascular procedures or neurovascular procedures.

BRIEF DESCRIPTION OF THE DRAWINGS

FIGS. 4a and 4b are fragmentary cross-sectional views of different manners of joining the extended crimpable section to the main body portion at the proximal portion of the guidewire assembly of FIG. 3a.

FIGS. 11 and 12 are side views of alternate embodiments of the guidewire assembly shown in FIG. 3a.

DETAILED DESCRIPTION OF THE PREFERRED EMBODIMENTS

Figure 1:
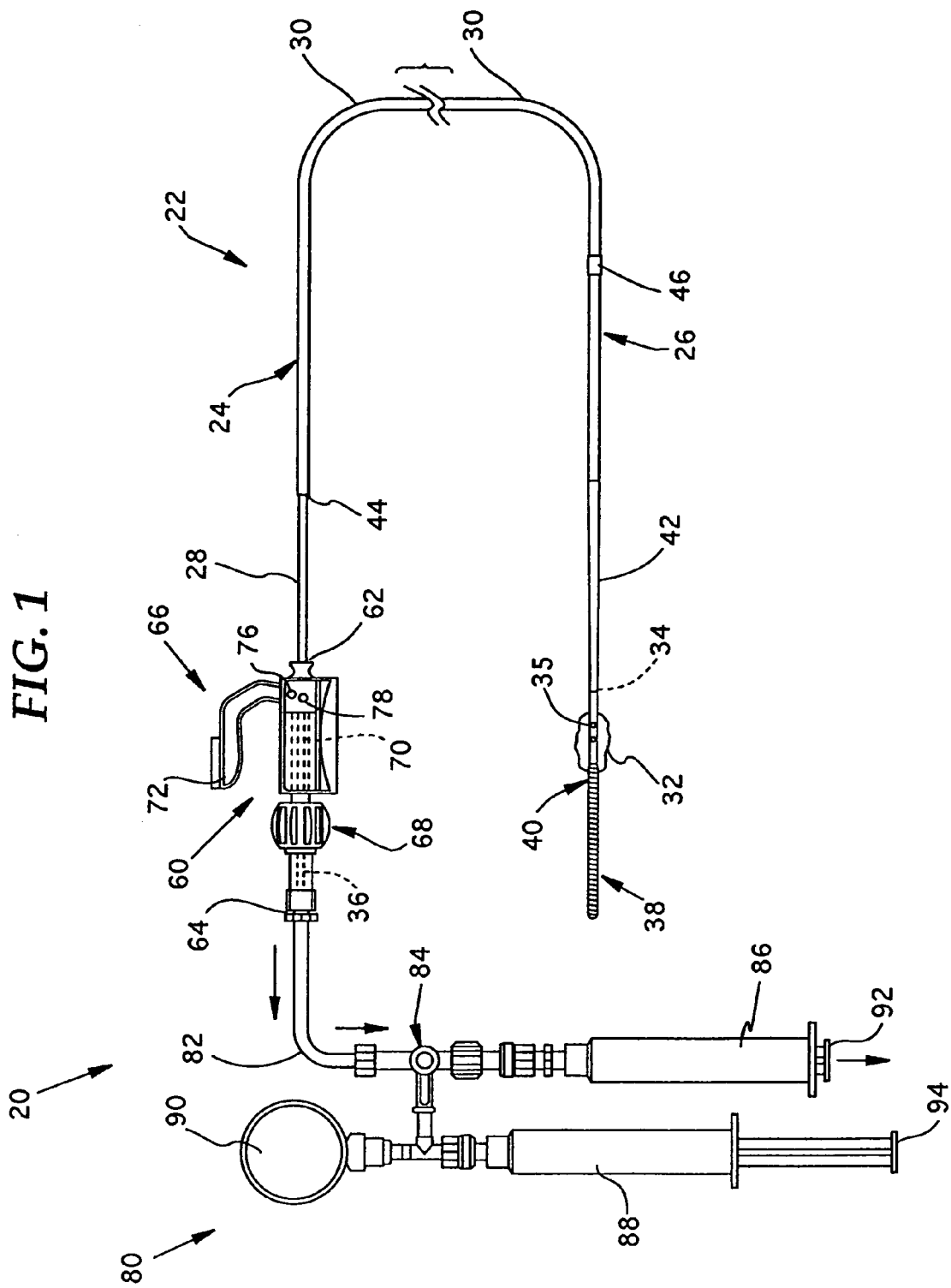
FIG. 1 is a schematic diagram of a guidewire occlusion system incorporating the present invention and operating in an evacuation mode.
Figure 2:
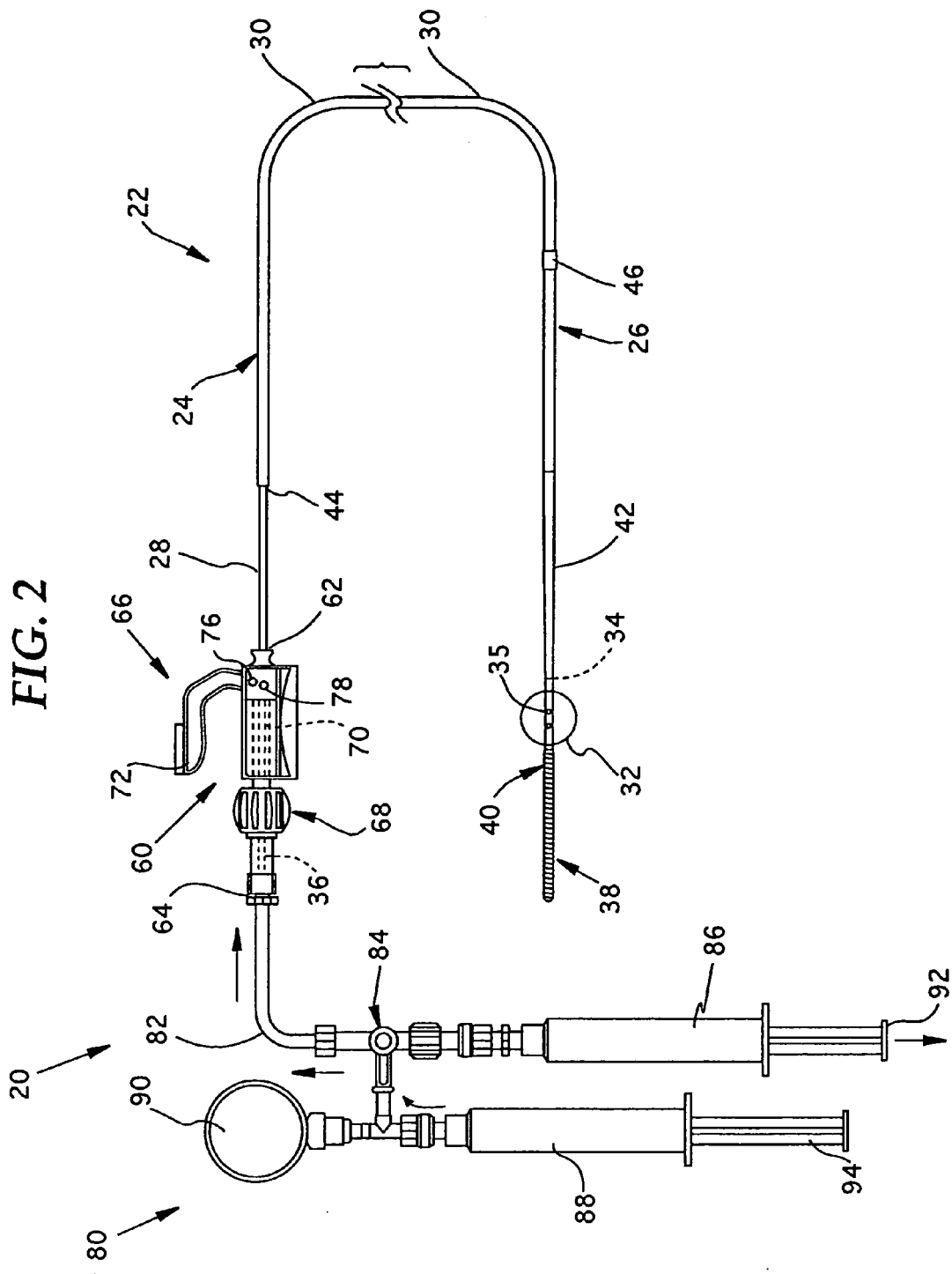
FIG. 2 is a schematic diagram of the guidewire occlusion system shown in FIG. 1 operating in an inflation mode.
Figure 3A:
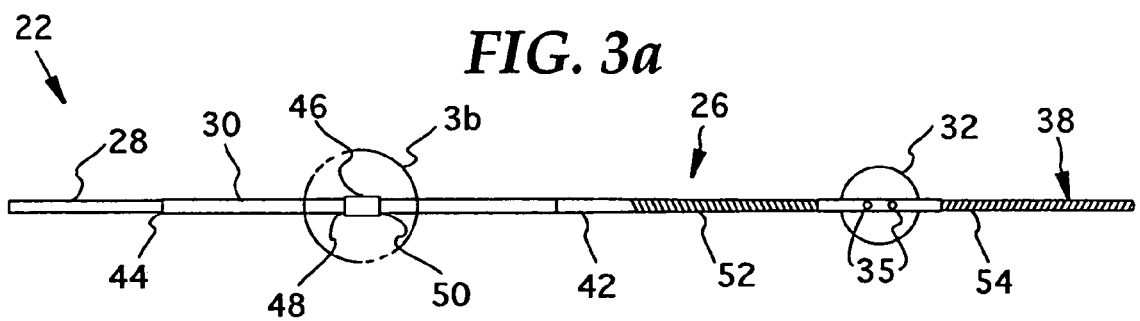
FIG. 3a is a side view of the guidewire assembly shown in FIG. 1.
Figure 3B:
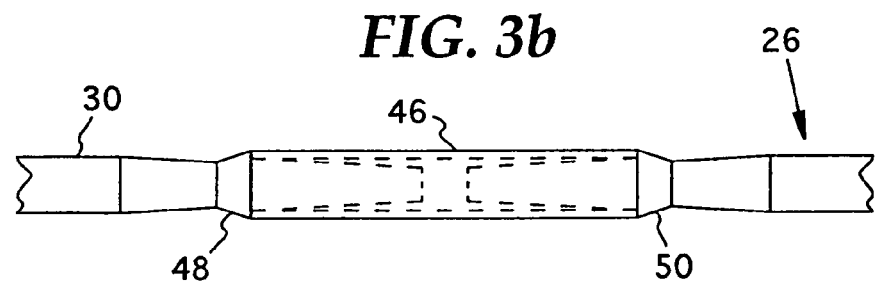
FIG. 3b is an enlarged view of the portion of FIG. 3a delineated by the circle 3b.

Referring now to FIGS. 1–2, the overall structure and operation of a guidewire occlusion system 20 incorporating the present invention will be described. The guidewire occlusion system 20 includes the guidewire assembly 22 of the present invention, a sealing system 60, and a gas inflation/evacuation system 80.

Guidewire assembly 22 is a tubular member that includes a proximal portion 24 and a distal portion 26. As used in the present invention, the terms proximal and distal will be used with reference to an operator, such that a distal portion of the guidewire assembly 22, for example, is the portion first inserted into a blood vessel, and the proximal portion remains exterior to the patient and is therefore closer to the operator. An extended crimpable section 28 is provided proximate the proximal portion 24 of guidewire assembly 22. In accordance with the present invention, the extended crimpable section 28 is comprised of a tubular segment having an outer diameter smaller than an outer diameter of a main body portion 30 of guidewire assembly 22. Although the diameter of the extended crimpable section 28 could be any size consistent with effective use as a guidewire, it will be understood that the smaller diameter allows for less force to be used in sealing the extended crimpable section 28 and provides a crimped seal that is not too large when crimped. An occlusive balloon 32 is located along the distal portion 26 of guidewire assembly 22, with channels or holes 35 allowing for fluid communication between a lumen 34 and the occlusive balloon 32. The occlusive balloon 32 is fluidly connected via the lumen 34 to the proximal end 36 of guidewire assembly 22. In a preferred embodiment, a flexible tip 38 is positioned at the distal end 40 of distal portion 26 of the guidewire assembly 22. Preferably, distal portion 26 of guidewire assembly 22 includes a tapered portion 42 to increase the flexibility and transition properties of the distal portion 26 of guidewire assembly 22.

Preferably, sealing system 60 is implemented as part of a handheld apparatus that also includes gas inflation/evacuation system 80. Alternatively, sealing system 60 may be a handheld unit completely separate from the gas inflation/evacuation system 80. Sealing system 60 includes a first aperture 62 into which the proximal end 36 of guidewire assembly 22 is insertable so as to operably position at least a portion of extended crimpable section 28 in relation to sealing system 60. Sealing system 60 further includes a second aperture 64 that is fluidly connectable to gas inflation/evacuation system 80. The sealing system 60 includes means for selectively sealing the extended crimpable section which in the preferred embodiment comprises a crimping mechanism 66 and a sealing mechanism 68. A passageway 70 is defined from first aperture 62 to second aperture 64 and extends through both crimping mechanism 66 and sealing mechanism 68. Preferably, at least a portion of the extended crimpable section 28 is inserted into first aperture 62 a sufficient distance to engage crimping mechanism 66 and sealing mechanism 68.

Figure 8:
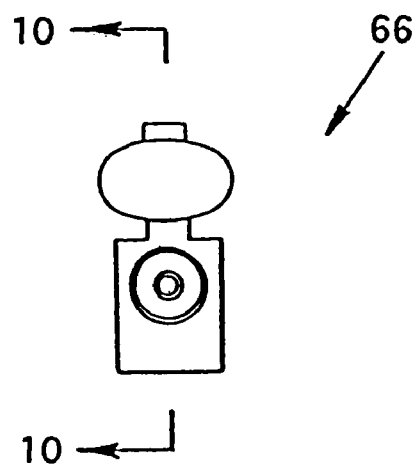
FIG. 8 is an end view of a crimping mechanism.
Figure 9:
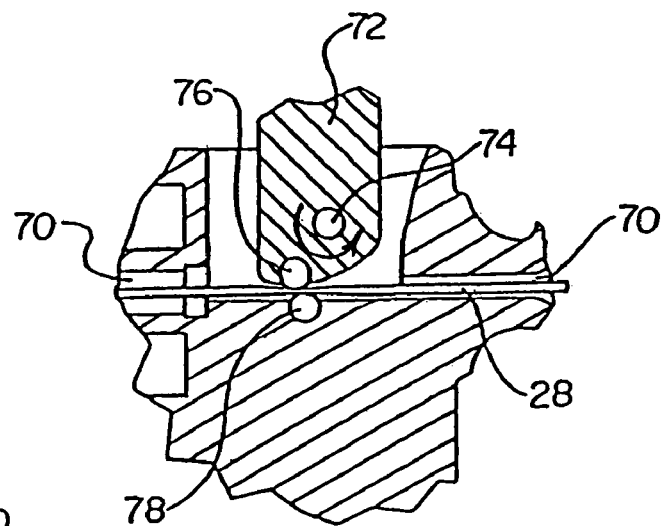
FIGS. 9 and 10 are two sectional views of the crimping mechanism of FIG. 8, FIG. 10 being a view taken along the line 10—10 of FIG. 8, and FIG. 9 being a magnification of the portion of FIG. 10 indicated by the dashed circle.
Figure 10:
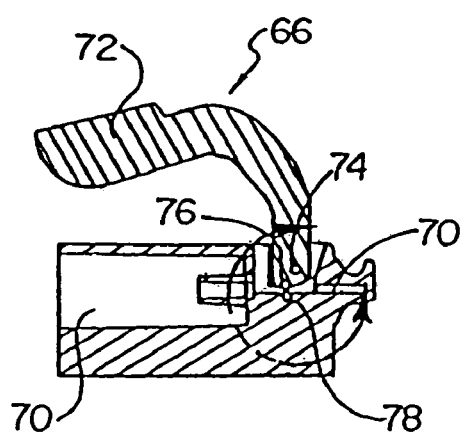

In a preferred embodiment of the crimping mechanism 66 as shown in FIGS. 8–10, the crimping mechanism 66 comprises a handle 72 that actuates a pivotable cam arrangement 74 that crimps and then severs the extended crimpable section 28 between a pair of rollers 76, 78 by mechanically flattening and pinching the extended crimpable section 28 to the point of breaking. Preferably, the sealing mechanism 68 has a rotatable hemostatic valve positioned proximal to the crimping mechanism 66 along passageway 70. Preferably, crimping mechanism 66 and sealing mechanism 68 are arranged coaxially with each other along a straight portion of passageway 70. In this embodiment, when the proximal end 36 of guidewire assembly 22 is inserted into first aperture 62 until the proximal end 36 engages the hemostatic valve of sealing mechanism 68, the extended crimpable section 28 is properly positioned relative to the crimping mechanism 66.

It will be seen that the relative distance between the engaging portions of sealing mechanism 68 and crimping mechanism 66 in this embodiment effectively defines the relative distances between a plurality of locations along extended crimpable section 28 at which an airtight seal can be created, as shown in FIGS. 1–2. To permit multiple inflations and deflations of the occlusive balloon 32 of the guidewire assembly 22, the length of the extended crimpable section 28 should be greater than at least twice the distance between crimping mechanism 66 and sealing mechanism 68.

The gas inflation/evacuation system 80 is connected via conduit 82 to the second aperture 64 of the sealing system 60. The gas inflation/evacuation system 80 preferably includes a valve arrangement 84 that selectively couples one of an evacuation system which includes means for evacuating the guidewire assembly and an inflation system which includes means for introducing a gas into the guidewire assembly to the conduit 82. The evacuation system includes an evacuation syringe 86 which is used to evacuate the guidewire assembly 22, passageway 70, and conduit 82. The inflation system includes an inflation syringe 88 which contains a volume of a gas sufficient to inflate the occlusive balloon 32 a plurality of times. Optionally, a pressure gauge 90 can be associated with the inflation syringe 88.

Preferably, the gas is a biocompatible gas such as carbon dioxide. Other biocompatible gasses that may be utilized with the present invention include oxygen, nitrogen, and nitrous oxide. While non-biocompatible gasses could be used, biocompatible gasses that are soluble in blood are preferred so as not to cause gas embolization in the event of a leak in the gas inflation/evacuation system. Preferably, the biocompatible gas also has a good driving gradient in addition to being soluble, in that the biocompatible gas will effectively go into a solution, in this case blood, better than ambient air. Although not preferred, low viscosity biocompatible liquids or foams also may be used for inflation provided the surface tension of the fluid is sufficient to permit the rapid inflation and deflation contemplated by the present invention.

It will be understood that if the guidewire assembly 22, including the occlusive balloon 32, could be verified as being capable of repeated inflations and deflations without any leakage or bursting of the occlusive balloon, then the evacuation portion of the gas inflation/evacuation system 80 would not be necessary, as the evacuation portion of the gas inflation/evacuation system 80 is intended for safety purposes to ensure that air within the guidewire assembly 22 and sealing system 60 is not introduced into the blood stream in the event of a failure, leakage or bursting of any component. For a more detailed description of the preferred embodiment of the sealing system 60 and the gas inflation/evacuation system, reference is made to the previously identified co-pending application Ser. Nos. 10/012,903 and 10/007,788 respectively entitled "Guidewire Occlusion System Utilizing Repeatably Inflatable Gas-Filled Occlusive Device" and "Gas Inflation/Evacuation System and Sealing System for Guidewire Assembly Having Occlusive Device."

Figure 4A:
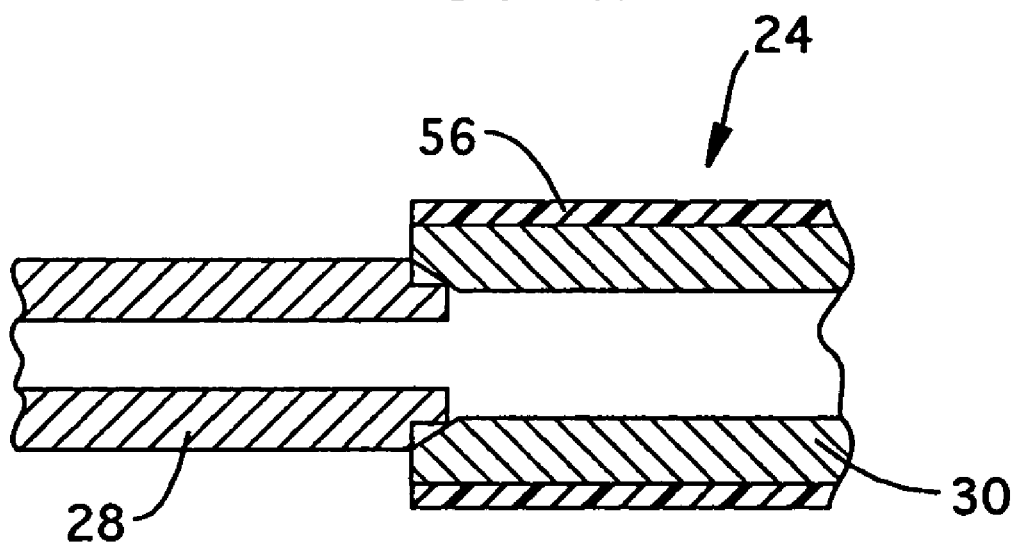
Figure 4B:
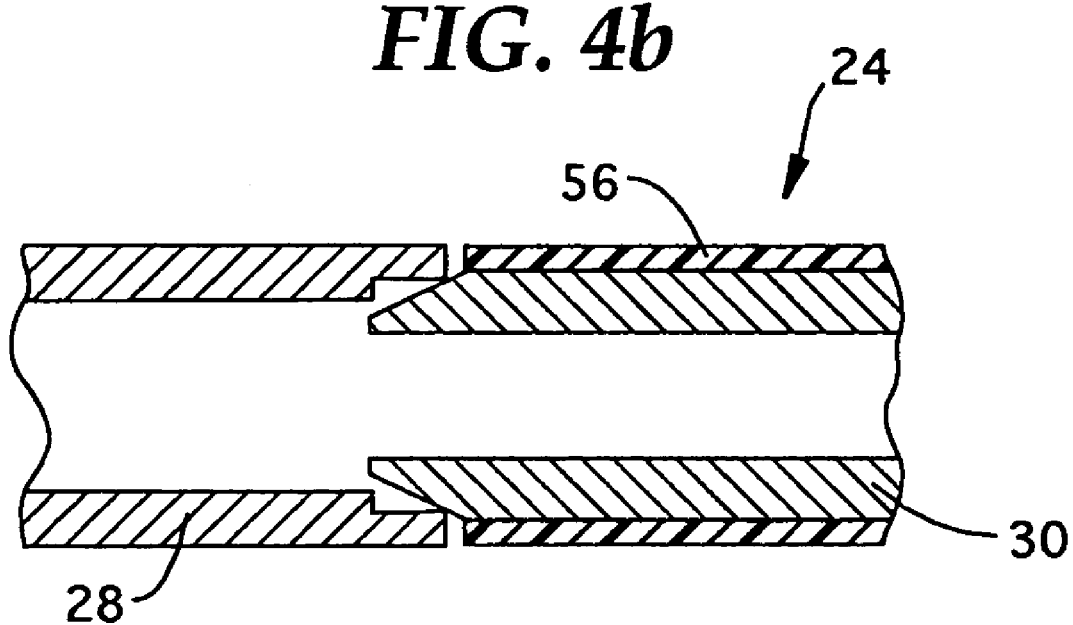

In a preferred embodiment shown in FIGS. 3a, 3b, 4a, and 4b, the main body portion 30 of the guidewire assembly 22 is formed of a primary stainless steel hypotube having an outer diameter of 0.013 inch and an inner diameter of 0.007 inch. To accomplish passive deflation in the desired time of less than one minute when the extended crimpable section 28 is cut, it is preferable that the main body portion 30 have an inner diameter of at least 0.002 inch. The extended crimpable section 28 of guidewire assembly 22 is comprised of a crimp tube also formed of stainless steel and having an outer diameter of 0.009 inch to 0.015 inch and an inner diameter of at least 0.002 inch and preferably about 0.005 inch. The extended crimpable section 28 is preferably a separate piece secured to the proximal portion 24 by a laser weld 44 (see FIGS. 1, 2 and 3a) of sufficient strength. Alternatively, the extended crimpable section 28 may be formed by centerless grinding or reducing the outer diameter of a portion of the proximal portion 24 of the main body portion 30 of guidewire assembly 22. Still other embodiments may enable the extended crimpable section to be a modified, treated or otherwise fabricated portion of the proximal portion 24 of the main body portion 30 of guidewire assembly 22 that is suitable for the particular sealing technique to be used. As shown in FIG. 4a, in one embodiment the distal end of the extended crimpable section 28 is preferably centerless ground and press fit within a chamfered proximal end of the main body portion 30. Alternatively, as shown in FIG. 4b, a chamfered crimp arrangement could be used. Still further, a separate joining/crimping tube or other tubular joining arrangements could be used. Preferably, a protective polymer coating 56 of polytetrafluoroethylene (PTFE) or a hydrophilic coating is applied by any of a number of known techniques such that the coating 56 surrounds the main body portion 30. The protective polymer coating 56 is preferably about 0.0004+/− 0.0003 inch thick such that the effective outer diameter of the main body portion 30 of guidewire assembly 22 is 0.0132–0.0144 inch.

In this embodiment, the extended crimpable section 28 can be made of any material that when deformed and severed retains that deformation so as to form an airtight seal. When crimped and severed, it is preferable that the extended crimpable section 28 not present a sharp, rigid point that is capable of piercing a gloved hand. It has been found that as long as the preferred embodiment is not gripped within less than one inch of the proximal end of the extended crimpable section 28, the severed proximal end of the extended crimpable section 28 does not penetrate a standard surgical glove. In addition, the extended crimpable section 28 must have sufficient strength in terms of high tensile and kink resistance to permit catheter devices to repeatedly pass over the extended crimpable section 28.

Figure 6:
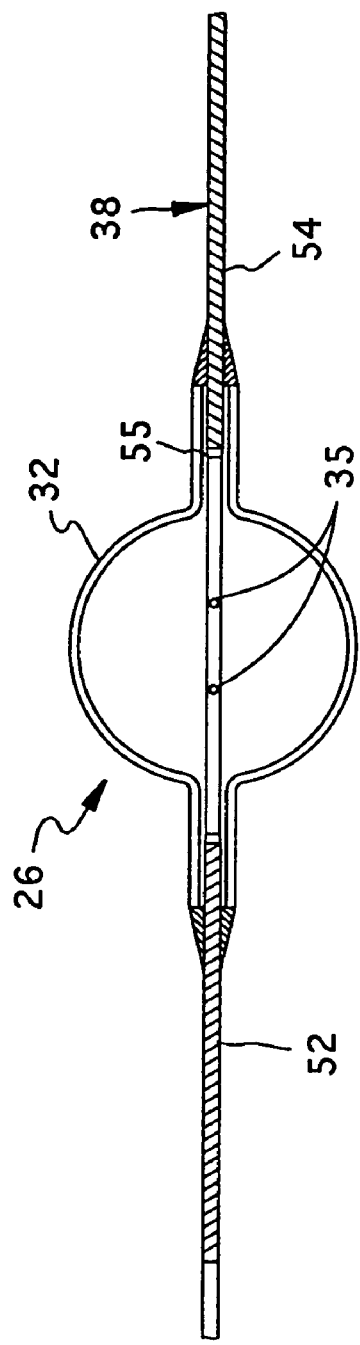
FIGS. 6 and 7 are side views of the distal portion of the guidewire assembly.
Figure 7:
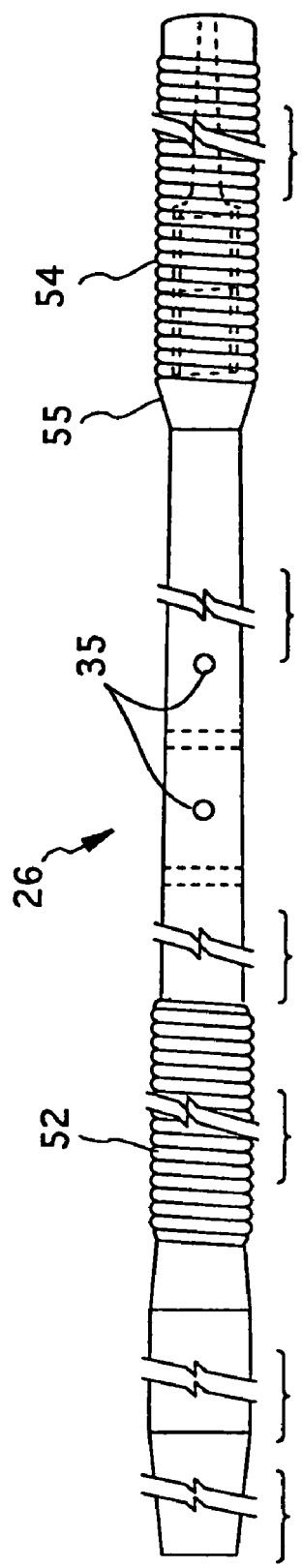

In this embodiment, the main body portion 30 is preferably secured to the distal portion 26 using a Ni—Ti or stainless steel sleeve 46 laser welded to the main body portion 30 at laser weld 48 and crimped to the distal portion 26 at crimp 50. The distal portion 26 is preferably formed of a Ni—Ti alloy having an inner diameter of 0.0045 inch and an outer diameter that ranges from 0.014 inch to 0.0075 inch to form tapered portion 42, preferably formed by a centerless grinding process. Preferably, the distal portion includes a pair of coil sections, proximal tip coil 52 and distal tip coil 54, that are longitudinally spaced apart and adjacent to the holes 35 and that assist in providing a better surface for bonding the occlusive balloon 32 to the distal portion 26. FIGS. 6 and 7 provide detailed views of this embodiment. This arrangement also tends to increase the visibility of the location of the occlusive balloon 32 under fluoroscopy, as the occlusive balloon 32 filled with a biocompatible gas will be radiotranslucent when compared to the two coils 52 and 54. Alternatively, a platinum markerband could be located around the distal portion 26 just proximal to the occlusive balloon 32 to serve as a radiopaque/MRI marker. The flexible tip 38 is a coiled tip attached to distal portion 26 distal to occlusive balloon 32, preferably by a crimp 55 (FIGS. 6 and 7). Alternatively, a sleeve could be welded to the flexible tip 38, and the tapered portion 42 could then be inserted into this sleeve and crimped.

Alternatively, any number of other alloys or polymer materials and attachment techniques could be used in the construction of the guidewire assembly 22, provided the materials offer the flexibility and torque characteristics required for a guidewire and the attachment techniques are sufficiently strong enough and capable of making an airtight seal. These materials include, but are not limited to, Ni—Ti, 17-7 stainless steel, 304 stainless steel, cobalt superalloys, or other polymer, braided or alloy materials. The attachment techniques for constructing guidewire assembly 22 include, but are not limited to, welding, mechanical fits, adhesives, sleeve arrangements, or any combination thereof.

The occlusive balloon 32 may be made of any number of polymer or rubber materials. Preferably, the occlusive balloon is preinflated to prestretch it so that expansion is more linear with pressure. Preferably, the pressure supplied by gas inflation/evacuation system 80 is designed to stay well within the elastic limit of the occlusive balloon 32. A two-layer occlusive balloon arrangement, adding gas and/or liquid between balloon layers, may be used in an alternate embodiment to increase visibility of the distal end 40 of the distal portion 26 of the guidewire assembly 22 under fluoroscopy.

In practice, medical personnel gain entry to the vessel lumen prior to use of the guidewire occlusion system 20. The extended crimpable section 28 of the proximal portion 24 of guidewire assembly 22 is inserted into first aperture 62 and connected via sealing mechanism 68. The distal portion 26 of guidewire assembly 22 is inserted into the vessel lumen, and occlusive balloon 32 is inserted to a point distal to the vessel occlusion. Valve arrangement 84 is set for evacuation. Evacuation syringe plunger 92 of evacuation syringe 86 is slidably withdrawn removing any air from guidewire assembly 22. Valve arrangement 84 is then set for inflation. Inflation syringe plunger 94 of inflation syringe 88 is slidably advanced inserting a volume of an inert gas into guidewire assembly 22. The inert gas inflates occlusive balloon 32 as shown in FIG. 2. During inflation, the medical personnel monitor pressure gauge 90 to ensure that the inflation pressure does not exceed the burst rating of the occlusive balloon 32 and to gauge the relative size of the occlusive balloon 32 as it is inflated. Following inflation of occlusive balloon 32, crimping mechanism 66 is employed to crimp the extended crimpable section 28 of guidewire assembly 22, thereby sealing the guidewire assembly 22 to maintain the occlusive balloon 32 in an inflated state. Sealing mechanism 68 is released and the extended crimpable section 28 is removed from first aperture 62 such that the proximal portion 24 of the guidewire assembly 22 is free of mechanical or other obstructions and can function as a conventional guidewire. When the medical personnel decide to deflate the occlusive balloon 32, the extended crimpable section 28 is cut using a medical scissors or the like distal to the existing crimp in the extended crimpable section 28. When the medical personnel deem reinflation of the occlusive balloon 32 to be necessary, the extended crimpable section 28 of the proximal portion 24 is reinserted into first aperture 62. Sealing mechanism 68 is then reactivated and the evacuation/inflation process can be repeated. It will be understood that a crimping handle 72 may also be provided with a separate severing arrangement to cut the extended crimpable section 28. Alternatively, extended crimpable section 28 may be scored or otherwise weakened in selected locations to assist in crimping or severing, including severing by repeated bending back and forth at one of the scored locations. In another embodiment, the extended crimpable section 28 could be broken off rather than sheared by using a brittle metal for the extended crimpable section that aids in the severing of the extended crimpable section 28.

Figure 5:
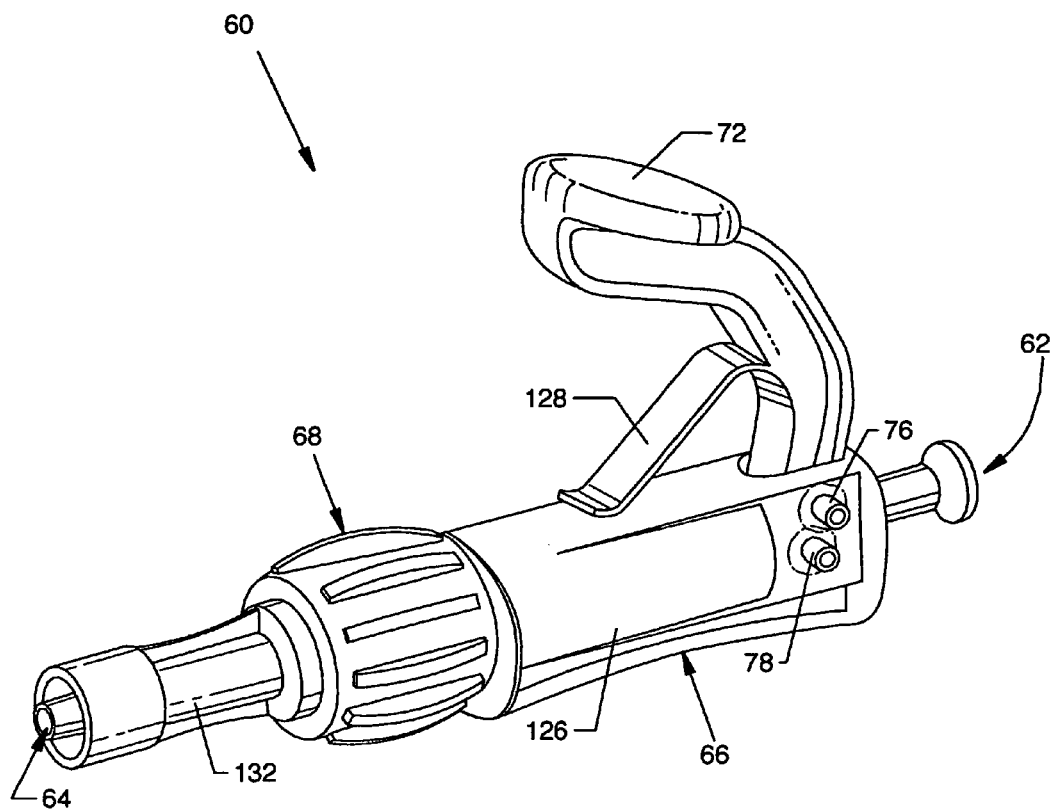
FIG. 5 is a perspective view of the sealing system.

FIG. 5 shows an embodiment of the sealing system. Specifically, FIG. 5 shows sealing system 60 which is comprised of sealing mechanism 68 and crimping mechanism 66. Crimping mechanism 66 is comprised of crimp body 126, handle 72, handle return 128, and first aperture 62. Sealing mechanism 68 is comprised of sealing body 132 and second aperture 64. Sealing system 60 has a passageway 70 (see FIGS. 1 and 2) fluidly interconnecting first aperture 62 and second aperture 64.

In practice, medical personnel gain access to the vessel lumen through which the guidewire assembly 22 will travel. The guidewire occlusion system 20 is removed from a biocompatible packaging. Flexible tip 38 is inserted in the vessel lumen and is manipulated to a point beyond the vessel occlusion. Valve arrangement 84 is adjusted to the evacuation position and evacuation syringe plunger 92 is slidably withdrawn to remove any gas present in the guidewire assembly 22. Valve arrangement 84 is then adjusted to the inflation position and inflation syringe plunger 94 is slidably inserted causing occlusive balloon 32 to inflate.

Following inflation of occlusive balloon 32, handle 72 of the crimping mechanism 66 is depressed causing roller 76 and roller 78 to crimp and preferably sever the extended crimpable section 28 of guidewire assembly 22. Severing of the extended crimpable section 28 serves as an immediate verification of the creation of an effective seal. Sealing mechanism 68 can be released and guidewire assembly 22 can be completely removed from the sealing system 60 allowing the occlusive balloon 32 to remain inflated while occlusive substance treatment occurs. Following treatment, the extended crimpable section 28 can be sheared or broken off, resulting in the deflation of the occlusive balloon 32. If occlusive treatment is complete, guidewire assembly 22 can be removed from the vessel lumen. If additional treatment is required, extended crimpable section 28 can be reattached to sealing system 60 through first aperture 62. Sealing mechanism 68 can be retightened and the evacuation/inflation process can be repeated.

In a preferred embodiment of the present invention, the guidewire assembly 22 is utilized as the guidewire for an atherectomy or thrombectomy procedure of the type described in U.S. Pat. Nos. 5,370,609 or 5,496,267, the disclosures of both of which are hereby incorporated by reference. In each of these procedures, the guidewire assembly 22 is introduced into the patient, the occlusive balloon 32 is inflated, and then the atherectomy or thrombectomy catheter arrangement is slid over the proximal end 36 of the guidewire assembly 22 and advanced until it is proximate and proximal to the location of the occlusive balloon. The procedure is performed for a time period consistent with the desired maximum length for blockage of the particular vessel, at which time the extended crimpable section 28 of the guidewire assembly 22 may be severed to deflate the occlusive balloon 32, thereby reestablishing blood flow within the vessel. Depending upon the nature of the procedure, the catheter arrangement may be removed from the vessel or left in place. Preferably, an evacuation of any plaque material or other debris dislodged by the therapy is accomplished before deflation of the occlusive balloon 32. The occlusive balloon 32 is reinflated prior to reinitiation of the procedure.

It will be understood that because gas is used as the inflation medium instead of liquid, the wall thickness and therefore the stiffness of tubular members of the guidewire assembly 22 can be increased to effectively match the stiffness and flexibility of an ideal solid guidewire. Stiffness increase is dramatic as a result because stiffness of the tube is governed by the equation $(R(o)^{}4-R(i)^{}4)$, such that an increase in wall thickness effectively quadruples the increase in stiffness of the guidewire assembly.

Rapid inflation and deflation of an occlusive balloon is the key to a successful occlusion device. The viscosity of the inflation fluid and resistance through the evacuation/inflation lumens dictate the effective speed of inflation and deflation. By lowering the viscosity of the inflation fluid, the present invention is able to increase the amount of resistance through the evacuation/inflation lumen that can be overcome. This results in being able to use a smaller inner diameter tube for the evacuation/inflation lumen which allows for a significant increase in the structural robustness of the guidewire assembly, while maintaining the desired inflation and deflation properties. The increase in allowable resistance also allows for the use of longer guidewire assemblies, specifically guidewire assemblies that are a more typical exchange length. With typical high viscosity inflation fluids used to inflate liquid occlusive balloons, for example, it is not practical to develop an exchange length guidewire assembly because of the long deflation times associated with evacuation of the high viscosity inflation fluid through a much longer lumen.

Figure 11:
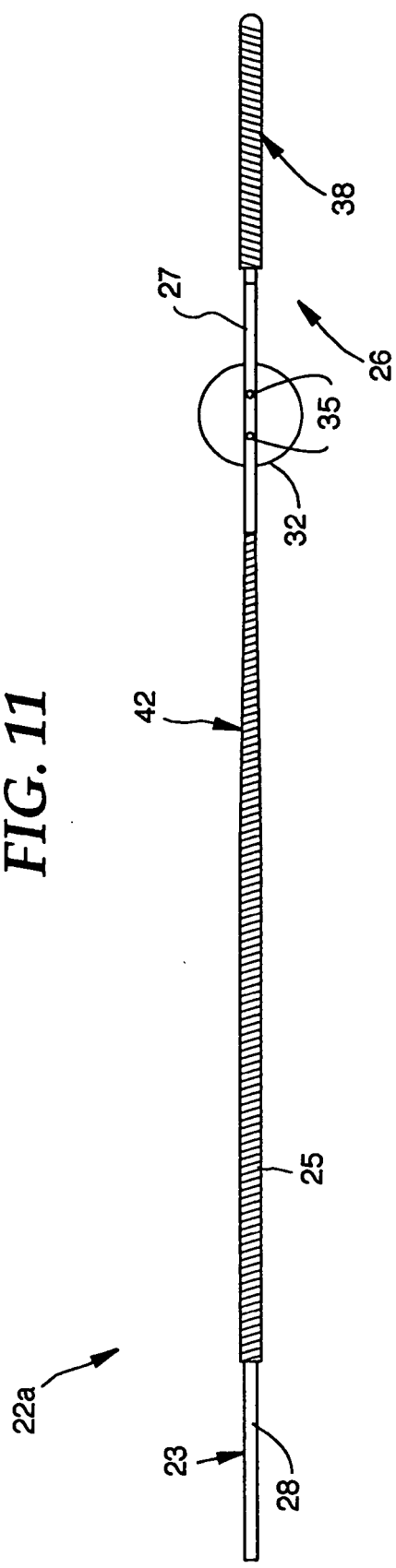

Another guidewire assembly embodiment is shown in FIG. 11 and is designated 22*a*. The guidewire assembly 22*a* includes a continuous stainless steel tube 23 of 0.007 inch outer diameter by 0.004 inch inner diameter having a wire 25 of 0.003 inch diameter wrapped therearound except for along the extended crimpable section 28 and, optionally, except for along a section 27 at the distal portion 26 of the continuous stainless steel tube 23. The distal portion 26 distal of the occlusive balloon 32 could be pinched in a taper to provide the desired flexible tip 38. One or more holes 35 are provided in the stainless steel tube 23 along section 27 over which the occlusive balloon 32 is positioned and adhesively secured. This embodiment would be less expensive by avoiding the use of Ni—Ti alloy and eliminating the need for laser welding or other attachment techniques along the guidewire assembly 22*a*.

Figure 12:
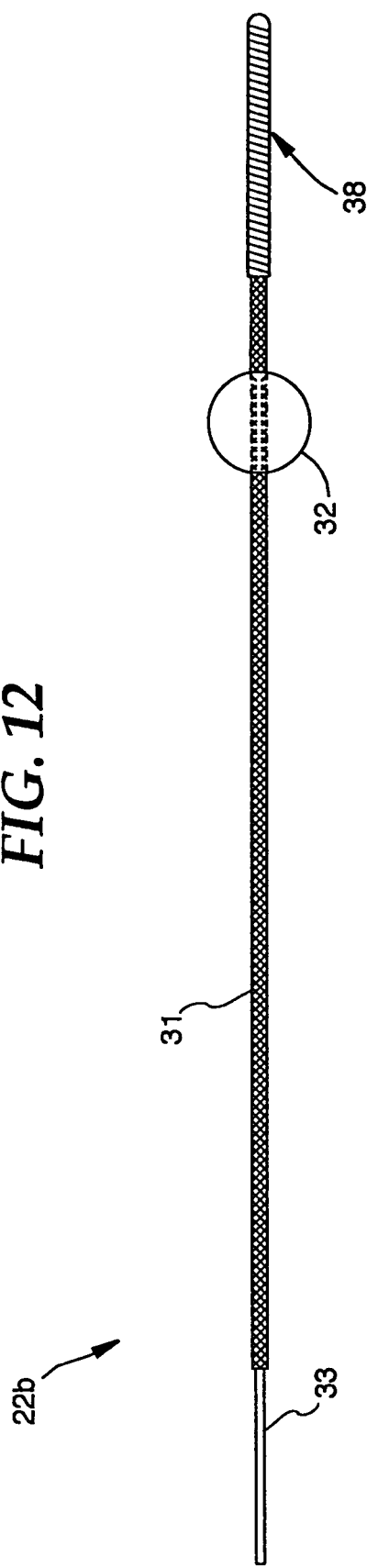

Another guidewire assembly embodiment is shown in FIG. 12 and is designated 22*b*. The guidewire assembly 22*b* includes a braided polyimide hypotube 31 having a tapered Ni—Ti core rod 33 positioned therein. The tapered Ni—Ti core rod 33 provides stiffness to the guidewire assembly 22*b*, but is much less expensive than a Ni—Ti tube. At least a proximal portion of the tapered Ni—Ti core rod 33 is tubular having a lumen defined therein and extending beyond a proximal end of the braided polyimide hypotube 31 to define the extended crimpable section. Alternatively, the braided polyimide hypotube 31 could include composite carbon fiber reinforcement to increase the strength thereof. Numerous arrangements for securing the tapered Ni—Ti core rod 33 within the braided polyimide hypotube 31 and for attaching the flexible tip 38 and the occlusive balloon 32 to the braided polyimide hypotube 31 are available with respect to this embodiment.

The present invention may be embodied in other specific forms without departing from the essential attributes thereof; therefore, the illustrated embodiments should be considered in all respects as illustrative and not restrictive, reference being made to the appended claims rather than to the foregoing description to indicate the scope of the invention.

| GUIDEWIRE ASSEMBLY HAVING OCCLUSIVE DEVICE AND REPEATABLY CRIMPABLE PROXIMAL END PARTS LIST | |
|---|---|
| 20 | guidewire occlusion system |
| 22 | guidewire assembly |
| 22a–b | guidewire assemblies |
| 23 | stainless steel tube |
| 24 | proximal portion |
| 25 | wire |
| 26 | distal portion |
| 27 | section |
| 28 | extended crimpable section |
| 30 | main body portion |
| 31 | braided polyimide hypotube |
| 32 | occlusive balloon |
| 33 | tapered Ni—Ti core rod |
| 34 | lumen |
| 35 | channel or hole |
| 36 | proximal end |
| 38 | flexible tip |
| 40 | distal end |
| 42 | tapered portion |
| 44 | laser weld |
| 46 | Ni—Ti or stainless steel sleeve |
| 48 | laser weld |
| 50 | crimp |
| 52 | proximal tip coil |
| 54 | distal tip coil |
| 55 | crimp |
| 56 | protective polymer coating |
| 60 | sealing system |
| 62 | first aperture |
| 64 | second aperture |
| 66 | crimping mechanism |
| 68 | sealing mechanism |
| 70 | passageway |
| 72 | handle |
| 74 | pivotable cam arrangement |
| 76 | roller |
| 78 | roller |
| 80 | gas inflation/evacuation system |
| 82 | conduit |
| 84 | valve arrangement |
| 86 | evacuation syringe |
| 88 | inflation syringe |
| 90 | pressure gauge |
| 92 | evacuation |

-continued

GUIDEWIRE ASSEMBLY HAVING OCCLUSIVE DEVICE AND
REPEATABLY CRIMPABLE PROXIMAL END
PARTS LIST

| | |
|---|---|
| | syringe plunger |
| 94 | inflation syringe plunger |
| 126 | crimp body |
| 128 | handle return |
| 132 | sealing body |

The invention claimed is:

1. A tubular guidewire assembly comprising:

a guidewire member having a distal end and a proximal end;

the guidewire member comprising an extended crimpable section proximate the proximal end and a main body portion distal of the extended crimpable section;

a lumen extending through the extended crimpable section and through the main body portion from the proximal end of the guidewire member and continuing to the distal end of the guidewire member;

an occlusive balloon proximate the distal end, the occlusive balloon being fluidly connected to the lumen so as to enable inflation and deflation of the occlusive balloon through the lumen upon respectively introducing and withdrawing fluid from the proximal end of the lumen;

the extended crimpable section being adapted to be selectively sealed with a permanent crimp at each of a plurality of separate locations to form successive airtight seals of the lumen to maintain the occlusive balloon inflated when it is in an inflated state, the extended crimpable section being dimensioned so as to be no larger in any outer diameter after being crimped than the largest outer diameter of any other portion of the tubular guidewire assembly; and, the extended crimpable section being quickly and reliably severable distal to each crimp to reopen the lumen to thereby provide for withdrawing fluid from the proximal end of the lumen and thereby deflate the occlusive balloon.

2. The tubular guidewire assembly of claim 1 wherein the guidewire assembly has an effective length of at least 40 cm and an outer diameter of the main body portion less than 0.060 inch, and wherein the extended crimpable section has an effective length of at least 1 cm and an outer diameter smaller than that of the main body portion and less than 0.050 inch.

3. The tubular guidewire assembly of claim 1 wherein the guidewire assembly has an effective length of at least 100 cm and an outer diameter of the main body portion less than 0.018 inch, and wherein the extended crimpable section has an effective length of at least 5 cm and an outer diameter smaller than that of the main body portion and less than 0.012 inch.

4. The tubular guidewire assembly of claim 1 wherein the extended crimpable section is dimensioned such that the largest outer diameter of the extended crimpable section after crimping is no greater than the largest outer diameter of the main body portion, and wherein the largest outer diameter of the extended crimpable section after crimping is less than a minimum inner diameter of a lumen of an intravascular device sized to be passed over the main body portion and tracked along the guidewire member to a treatment location.

5. The tubular guidewire assembly of claim 1 wherein the extended crimpable section has a length sufficient to permit a plurality of crimps and a plurality of corresponding cuts therealong and has an outer diameter that is smaller than the outer diameter of the main body portion of the guidewire member.

6. The tubular guidewire assembly of claim 1 wherein the main body portion is formed of a stainless steel hypotube.

7. The tubular guidewire assembly of claim 1 wherein the main body portion comprises a stainless steel hypotube and the extended crimpable section is collinearly attached to the proximal end of the stainless steel hypotube and is formed of a stainless steel hypotube having an outer diameter smaller than the outer diameter of the stainless steel hypotube of the main body portion.

8. The tubular guidewire assembly of claim 6 wherein the guidewire member further includes a distal portion formed of a Ni—Ti alloy.

9. The tubular guidewire assembly of claim 8 wherein the distal portion includes a tapered portion.

10. The tubular guidewire assembly of claim 9 wherein the tapered portion has an outer diameter that ranges from 0.014 inch to 0.0075 inch.

11. The tubular guidewire assembly of claim 8 wherein the distal portion includes a platinum markerband proximal to the occlusive balloon.

12. The tubular guidewire assembly of claim 8 further comprising a flexible coil tip attached to the distal portion distal to the occlusive balloon.

13. The tubular guidewire assembly of claim 1 wherein the occlusive balloon is capable of repeated inflation and deflation during a vascular procedure in between which the proximal end of the extended crimpable section is free of mechanical connections and obstructions thereby enabling the guidewire member to function as a conventional exchange guidewire with the largest outer diameter of the extended crimpable section being no larger than the outer diameter of the main body portion, regardless of whether the extended crimpable section is crimped or not crimped, so that an intravascular catheter can be passed over the extended crimpable section and the main body portion without interference.

14. The tubular guidewire assembly of claim 1 wherein the lumen has an inner diameter of at least 0.002 inch such that passive deflation of the occlusive balloon can be accomplished in less than one minute after crimping and subsequently severing a portion of the extended crimpable section.

15. The tubular guidewire assembly of claim 1 wherein the extended crimpable section is formed of a material and is dimensioned such that the extended crimpable section has sufficient strength in terms of high tensile and kink resistance to permit catheter devices to repeatedly pass over the extended crimpable section yet, when severed, the extended crimpable section does not penetrate a standard surgical glove when gripped within less than one inch of a proximate end of the extended crimpable section.

16. The tubular guidewire assembly of claim 1 wherein the occlusive balloon has been preinflated to prestretch it so that expansion of the occlusive balloon in use is relatively linear with pressure.

17. The tubular guidewire assembly of claim 1 wherein the extended crimpable section further comprises a plurality of scores which extend only partway through the wall of the extended crimpable section and weaken the extended crimpable section at a plurality of locations along the extended crimpable section to aid in severing the extended crimpable section at the scored locations.

18. The tubular guidewire assembly of claim 1 wherein the entire guidewire member is formed of a continuous stainless steel tube having a wire wrapped therearound except for along the extended crimpable section.

19. The tubular guidewire assembly of claim 1 wherein the guidewire member comprises a braided polyimide hypotube having a tapered core rod positioned therein.

20. The tubular guidewire assembly of claim 19 wherein at least a proximal portion of the tapered core rod is tubular having a lumen defined therein and extending proximate a proximal end of the braided polyimide hypotube to define the extended crimpable section.

21. The tubular guidewire assembly of claim 1 further comprising a pair of coils positioned along a distal portion of the guidewire member that are longitudinally spaced apart and adjacent to at least one hole in the guidewire member that provides fluid access between the lumen and the occlusive balloon, with at least a portion of the occlusive balloon being bonded to at least a portion of each of the pair of coils.

22. The tubular guidewire assembly of claim 1 wherein the extended crimpable section further comprises a plurality of weakened sections at a plurality of locations along the extended crimpable section to aid in severing the extended crimpable section at the locations of the weakened sections, there being no leakage of fluid at any weakened section unless the extended crimpable section has been severed at a weakened section.

23. A tubular guidewire assembly comprising:
a guidewire member having a proximal end and a distal end and including a main body portion with a lumen extending therethrough and an extended crimpable section with a lumen extending therethrough, the extended crimpable section being joined to the main body portion and extending from the main body portion to the proximal end of the guidewire member, the lumens of the main body portion and the extended crimpable section being in fluid communication with each other;

an occlusive balloon proximate the distal end of the guidewire member, the occlusive balloon being in fluid communication with the lumen of the main body portion and thereby in fluid communication with the lumen of the extended crimpable section so as to enable inflation of the occlusive balloon upon introduction of fluid into the lumens at the proximal end of the guidewire member and deflation of the occlusive balloon upon withdrawal of fluid from the lumens at the proximal end of the guidewire member;

the extended crimpable section being of sufficient length to enable the lumen therethrough to be repeatably selectively sealed airtight by flattening the extended crimpable section with successive permanent crimps at separate locations along its length to maintain the occlusive balloon inflated whenever it is in its inflated state; and, the extended crimpable section being structured so that it can be quickly and reliably severed distal to each successive permanent crimp to reopen its lumen and thereby provide for rapid deflation of the occlusive balloon.

* * * * *

UNITED STATES PATENT AND TRADEMARK OFFICE
CERTIFICATE OF CORRECTION

| | | |
|---|---|---|
| PATENT NO. | : 7,169,161 B2 | Page 1 of 1 |
| APPLICATION NO. | : 10/012891 | |
| DATED | : January 30, 2007 | |
| INVENTOR(S) | : Bonnette et al. | |

It is certified that error appears in the above-identified patent and that said Letters Patent is hereby corrected as shown below:

On the Title page at Item (75), delete "Kravic" and insert -- Kravik --, therefor.

In Column 5, Line 39, delete "cm" and insert -- 5 cm --, therefor.

Signed and Sealed this

Nineteenth Day of January, 2010

David J. Kappos
*Director of the United States Patent and Trademark Office*